(12) United States Patent
Takeuchi et al.

(10) Patent No.: US 7,288,069 B2
(45) Date of Patent: Oct. 30, 2007

(54) ULTRASONIC PROBE AND METHOD OF MANUFACTURING THE SAME

(75) Inventors: Takashi Takeuchi, Otawara (JP); Yasuharu Hosono, Yokohama (JP); Mamoru Izumi, Tokyo (JP); Yohachi Yamashita, Yokohama (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 102 days.

(21) Appl. No.: 09/778,071

(22) Filed: Feb. 7, 2001

(65) Prior Publication Data

US 2001/0041837 A1   Nov. 15, 2001

(30) Foreign Application Priority Data

Feb. 7, 2000   (JP) ............................. 2000-029309

(51) Int. Cl.
 *A61B 8/00* (2006.01)
(52) U.S. Cl. ..................... 600/459; 310/335
(58) Field of Classification Search ........ 600/437–471; 310/311–371; 367/140–190; 73/DIG. 4, 73/618–644; 29/25.35
See application file for complete search history.

(56) References Cited

U.S. PATENT DOCUMENTS

| | | | |
|---|---|---|---|
| 4,217,684 A * | 8/1980 | Brisken et al. ............. | 29/25.35 |
| 4,255,726 A * | 3/1981 | Kinoshita et al. ........... | 333/195 |
| 4,658,176 A * | 4/1987 | Nakaya et al. ............. | 310/334 |
| 4,680,499 A * | 7/1987 | Umemura et al. .......... | 310/334 |
| 4,683,396 A * | 7/1987 | Takeuchi et al. ........... | 310/358 |
| 4,756,808 A * | 7/1988 | Utsumi et al. .............. | 204/486 |
| 4,795,935 A * | 1/1989 | Fujii et al. .................. | 310/336 |
| 4,825,115 A * | 4/1989 | Kawabe et al. ............. | 310/327 |
| 5,115,810 A * | 5/1992 | Watanabe et al. ........... | 600/459 |
| 5,163,436 A * | 11/1992 | Saitoh et al. ............... | 600/459 |
| 5,290,408 A * | 3/1994 | Lewandowski et al. ..... | 204/153 |
| 5,295,487 A | 3/1994 | Saitoh et al. | |
| 5,311,095 A * | 5/1994 | Smith et al. ................ | 310/334 |
| 5,329,498 A * | 7/1994 | Greenstein .................. | 367/155 |
| 5,402,791 A | 4/1995 | Saitoh et al. | |
| 5,406,951 A * | 4/1995 | ten Hoff et al. ............ | 600/467 |
| 5,410,209 A | 4/1995 | Yamashita et al. | |

(Continued)

FOREIGN PATENT DOCUMENTS

JP   54-19151   7/1979

(Continued)

OTHER PUBLICATIONS

Shiroh Saitoh, et al., IEEE Trans. Of Ultrasonics, Ferr. and Freq. Cont., vol. 46, No. 2, 11 pages, "A 3.7 MHz Array Probe Using 0.9 $Pb(Zn_{1/3}Nb_{2/3})O_3$-$0.09PbTiO_3$ Single Crystal", Mar. 1999.

*Primary Examiner*—Francis J. Jaworski
(74) *Attorney, Agent, or Firm*—Oblon, Spivak, McClelland, Maier & Neustadt, P.C.

(57) ABSTRACT

An ultrasonic probe is characterized in that a piezoelectric member 111 formed of solution-based single-crystal containing at least plumbum titanate is sandwiched between resin layers 113 and 115 having smaller acoustic impedance than the piezoelectric member and having conductivity, so processing errors are prevented from occurring during cutting and the resin layers can be used as acoustic layers or electrodes.

10 Claims, 7 Drawing Sheets

U.S. PATENT DOCUMENTS

| | | | |
|---|---|---|---|
| 5,423,220 A * | 6/1995 | Finsterwald et al. | 73/642 |
| 5,457,863 A * | 10/1995 | Thomas et al. | 29/25.35 |
| 5,497,540 A * | 3/1996 | Venkataramani et al. | 29/25.35 |
| 5,605,154 A * | 2/1997 | Ries et al. | 600/444 |
| 5,884,627 A * | 3/1999 | Wakabayashi et al. | 600/447 |
| 5,920,523 A * | 7/1999 | Hanafy et al. | 367/140 |
| 5,923,115 A * | 7/1999 | Mohr et al. | 310/334 |
| 6,020,675 A | 2/2000 | Yamashita et al. | |
| 6,038,752 A * | 3/2000 | Finsterwald et al. | 29/25.35 |
| 6,049,159 A * | 4/2000 | Barthe et al. | 310/334 |
| 6,091,180 A * | 7/2000 | Unami et al. | 310/328 |
| 6,104,126 A * | 8/2000 | Gilmore | 310/334 |
| 6,121,718 A * | 9/2000 | Mohr, III | 310/334 |
| 6,124,664 A * | 9/2000 | Mamayek et al. | 310/327 |
| 6,160,340 A * | 12/2000 | Guo et al. | 310/334 |
| 6,255,761 B1 * | 7/2001 | Benjamin | 310/334 |
| 6,308,389 B1 * | 10/2001 | Tezuka | 29/25.35 |
| 6,323,061 B1 * | 11/2001 | Sakazaki et al. | 438/113 |
| 6,551,247 B2 * | 4/2003 | Saito et al. | 600/459 |
| 6,551,248 B2 * | 4/2003 | Miller | 600/459 |
| 6,558,323 B2 * | 5/2003 | Wakabayashi et al. | 600/437 |
| 6,575,956 B1 * | 6/2003 | Brisken et al. | 604/500 |
| 7,224,104 B2 * | 5/2007 | Shibamoto et al. | 310/335 |

FOREIGN PATENT DOCUMENTS

| | | |
|---|---|---|
| JP | 57-45290 | 3/1982 |
| JP | 58-21883 | 2/1983 |
| JP | 60-54600 | 3/1985 |
| JP | 60-85699 | 5/1985 |
| JP | 60-97800 | 5/1985 |
| JP | 61-53562 | 3/1986 |
| JP | 61-109400 | 5/1986 |
| JP | 62-122499 | 6/1987 |
| JP | 62-131700 | 6/1987 |
| JP | 8-280674 | 10/1996 |
| JP | 9-84194 | 3/1997 |
| JP | 9-214014 | 8/1997 |
| JP | 11-155859 | 6/1999 |
| JP | 11-318902 | 11/1999 |
| JP | 2000-14672 | 1/2000 |

* cited by examiner

DIRECTION OF SLICE

DIRECTION OF ARRAY

ULTRASONIC PROBE AND METHOD OF MANUFACTURING THE SAME

CROSS-REFERENCE TO RELATED APPLICATIONS

This application is based upon and claims the benefit of priority from the prior Japanese Patent Application No. 2000-029309, filed Feb. 7, 2000, the entire contents of which are incorporated herein by reference.

BACKGROUND OF THE INVENTION

The present invention relates to an ultrasonic probe for used in an ultrasonic diagnosis apparatus, an ultrasonic treatment apparatus, and the like, and a method of manufacturing the probe.

An ultrasonic probe is constructed with a piezoelectric member used as a main member, emits an ultrasonic wave to a target object, and receives reflection waves from interfaces between which acoustic impedance differs, thereby to image the inner state of the target object. As an ultrasonic imaging apparatus which adopts this kind of ultrasonic probe, for example, there is a medical diagnosis apparatus for inspecting inside of a human body, an inspection apparatus for the purpose of flaw detection inside metal welding, or the like.

In the ultrasonic diagnosis apparatus as the medical ultrasonic imaging apparatus, photographing techniques such as a color flow mapping (CFM) method in which Doppler shift of ultrasonic waves depending on blood flow is used to display two-dimensionally the speed of blood flow, a tissue harmonic imaging (THI) method in which a two-dimensional wave is imaged, and the like have been developed in addition to a stratigraphic image (B-mode image) of a human body. The ultrasonic probe has a form which coincides with these various photographing methods and enables transmission/reception of ultrasonic waves concerning all organs of a human body.

In general, it is demanded that the ultrasonic probe for use in an ultrasonic diagnosis apparatus can obtain an image with a high resolution with a high sensitivity. This is because small pathologies and gaps can be detected by an image capable of displaying clearly a deep part of a diagnosis target. In recent years, consideration has been taken into heightening of the sensitivity and widening of the band of the ultrasonic probe as a sensor part.

To achieve a higher sensitivity and a wider band as described above, studies are made on a composite piezoelectric member such as a structure in which a piezoelectric column or piezoelectric particles are embedded in resins. For example, structures thereof are proposed in Japanese Patent Application KOKOKU Publication No. 54-19151 and Japanese Patent Application KOKAI Publication Nos. 60-97800, 61-53562, and 61-109400 and the like, and manufacturing methods thereof are proposed in Japanese Patent Application KOKAI Publication Nos. 57-45290, 58-21883, 60-54600, 60-85699, 62-122499, and 62-131700 and the like.

An ultrasonic probe using a composite piezoelectric member disclosed in these references has merits that the acoustic impedance decreases close to the impedance of a living body and that the electromechanical coupling factor in the structure of 1-3 type, 2-2 type, or the like increases in comparison with a thin plate. This is because PZE-based piezoelectric ceramics having a large dielectric constant and a large electromechanical coupling factor $k_{33}$ are used mainly.

Meanwhile, an ultrasonic probe using a composite piezoelectric member has a problem that the electromechanical coupling factor improves less compared with a reduction of the dielectric constant due to inclusion of resins. In practice, the composite piezoelectric member is used only for a single-type mechanical probe, an annular array, or the like which has a large element area. Hence, trials have been made to solve this problem by using a solution-based piezoelectric single-crystal (Japanese Patent Application KOKAI Publication No. 09-84194).

To realize an ultrasonic probe with high sensitivity and a wide band, there has been a method of forming a composite piezoelectric member 30 made of solution-based piezoelectric single-crystal 32 and resins 34 and 36, like the array-type probe shown in FIG. 1A. However, formation of this composite piezoelectric member 30 has a problem of an error in cutting work. That is, solution-based piezoelectric single-crystal 32 generally has low breakdown resistance and is fragile, so a problem occurs in that chipping is caused in cutting work for forming a kerf 38 shown in FIG. 1B into an array-like shape. This chipping causes characteristic deterioration and cracks in an element, thereby causing errors.

Hence, we have proposed a structure as shown in FIG. 1D (Japanese Patent Application KOKAI Publication No. 2000-14672) as an ultrasonic probe using single crystal of this kind, and have tried to improve the probe manufacture yield. FIG. 1D shows a cross-sectional view structure of an array probe using a single-crystal vibration element. Electrodes 4 and 5 are formed on both sides of the single-crystal vibration element 1, and a backing material 2 is provided on the lower surface of the vibration element 1. In addition, acoustic matching layers 3a and 3b are formed on the single-crystal vibration element, so that the single-crystal vibration element 1 and the matching layers 3a and 3b are subjected to array processing. The array pitch of the array probe is about 0.1 mm in case where the pitch is small. Further, transmission/reception of an ultrasonic wave is carried out through an acoustic lens 8 provided on the acoustic matching layer 3b. The electrodes 4 and 5 formed on the both surfaces of the single-crystal vibration element 1 are connected to a cable through FPCs 6 and 7 and thus connected to a diagnosis apparatus (omitted from figures). In the structure shown in FIG. 1D, the FPC 6 is joined to the vibration element by an epoxy-based adhesion throughout the all surface of the vibration element, by extending the conductive layer of the FPC so as to correspond to the area of the vibration element. Metal Cu is generally used as the conductive layer. FIG. 1E shows a conductive layer at a lower portion of the signal FPC shown in FIG. 1D, viewed from the single-crystal vibration element 1. The conductive layer 6a' of the signal FPC shown in FIG. 1D is led like a hound's tooth check as shown in FIG. 1E. This array structure is prepared in the manner explained below. Electrodes 4 and 5 are formed on the single-crystal vibration element 1 having an integral shape. A vibration element to which a FPC is adhered is adhered to the backing member 2. Acoustic matching layers 3a and 3b are formed, and thereafter, a dicing saw is used to cut them from the side of the matching layer. Thereafter, the acoustic lens 8 is formed on the acoustic matching layer 3, and preparation is thus completed.

However, a problem has occurred in that cracking and chipping occur in some cases at the dicing edge part of the surface where the FPC of the single-crystal vibration element is adhered, if the above manufacturing method is adopted, a FPC whose conductive layer is extended to correspond to the area of the single-crystal vibration element is adhered to the entire surface of the vibration element by an epoxy-based adhesion, the vibration element is adhered to a backing member by an epoxy adhesion, an acoustic layer is formed on the vibration element, and array processing is thereafter carried out by a dicing saw. This is considered to occur because the piezoelectric single-crystal having weak mechanical strength and the conductive layer having a deteriorated cutting characteristic are cut simultaneously. In addition, burs from the conductive layer which are created during processing roughen the cutting surface of the single-crystal vibration element, and cutting wastes caught under a blade are factors which lower the cutting characteristic. These cracking and chipping of the single-crystal vibration element are difficult to suppress even if the processing conditions are adjusted. Large cracking causes a disconnection error and lowers the manufacturing yield while small cracking expands during use and may cause a market accident. Also, chipping reduces the electrode area of the vibration element processed into a strip-like shape, so that not only characteristic deterioration is involved but also characteristic variants increase between array elements. Since several tens to several hundreds of array elements are used, characteristic variants between array elements influence the image quality of a stratigraphic image.

BRIEF SUMMARY OF THE INVENTION

The present invention has been made to solve the above problems, and has an object of providing one-dimensional and two-dimensional array ultrasonic probes which do not cause processing errors during cutting by using a composite piezoelectric member of solution-based piezoelectric single-crystal and resins, and a method of providing the ultrasonic probes.

The present invention comprises features as follows.

According to the first aspect of the present invention, there is provided an ultrasonic vibration element comprising: a single-crystal piezoelectric member cut like an array; and at least one of an upper resin layer formed on an upper surface of the piezoelectric member and having smaller acoustic impedance than the piezoelectric member, and a lower resin layer formed on a lower surface of the piezoelectric member and having smaller acoustic impedance than the piezoelectric member, wherein the at least one of the upper resin layer and the lower resin layer has an excellent cutting characteristic and conductivity and functions as an electrode.

According to the second aspect of the present invention, there is provided an ultrasonic probe comprising an ultrasonic vibration element constructed by a 1-3 or 2-2 type composite piezoelectric member including a piezoelectric member formed of solution-based single-crystal containing at least plumbum titanate, and at least one of an upper resin layer formed on an upper surface of the piezoelectric member and having smaller acoustic impedance than the piezoelectric member, and a lower resin layer formed on a lower surface of the piezoelectric member and having smaller acoustic impedance than the piezoelectric member, wherein the at least one of the upper resin layer and the lower resin layer has an excellent cutting characteristic and conductivity and functions as an electrode.

In the probe according to the second aspect, the at least one of the upper resin layer and the lower resin layer has acoustic impedance of $2\times10^6$ g/m² to $10\times10^6$ g/m² and functions as an acoustic matching layer.

According to the third aspect of the present invention, there is provided a method of manufacturing an ultrasonic probe, comprising: a first step of forming a resin layer on at least one of upper and lower surfaces of a single-crystal piezoelectric member, the resin layer having smaller acoustic impedance than the single-crystal piezoelectric member; a second step of cutting the single-crystal piezoelectric member and the resin layer, thereby to form a plurality of kerfs; and a third step of filling the plurality of kerfs with resins.

In the method according to the third aspect, the plurality of kerfs are formed like a grid in the second step. In addition, the method may be structured to comprise a fourth step of polishing the resin layer to remove the resin layer.

According to the fourth aspect of the present invention, there is provided a method of manufacturing an ultrasonic probe, comprising: a first step of adhering a plurality of single-crystal piezoelectric members to a resin sheet; a second step of cutting the piezoelectric single-crystal members and the resin sheet, thereby to form a plurality of kerfs; and a third step of filling the plurality of kerfs with resins.

According to the fifth aspect of the present invention, there is provided an ultrasonic probe comprising: a plurality of piezoelectric members formed of solution-based single-crystal containing at least plumbum titanate, and arranged like an array; a first electrode formed on a lower surface of each of the piezoelectric members; and a first flexible printed wiring board having a plurality of pattern wires each having a width smaller than a width of each of the piezoelectric member in an array direction, for leading and connecting an electric wire from each of the first electrode to an ultrasonic diagnosis apparatus body.

The probe according to the fifth aspect further comprises: a second electrode formed on an upper surface of each of the piezoelectric members; and a second flexible printed wiring board having a plurality of pattern wires each having a width smaller than a width of each of the piezoelectric member in an array direction for leading and connecting an electric wire from each of the second electrode to ground.

According to the invention having structures as described above, it is possible to manufacture an ultrasonic probe which does not cause processing errors during cutting. As a result, an ultrasonic probe can be realized with high sensitivity and a wide band characteristic.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the present invention.

DETAILED DESCRIPTION OF THE INVENTION

In the following, first to seventh embodiments of the present invention will be explained with reference to the drawings.

FIRST EMBODIMENT

Figure 1A:
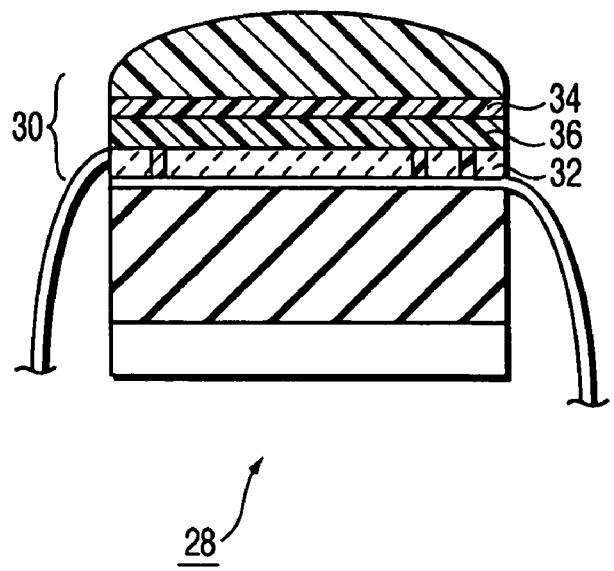
FIGS. 1A and 1D are views showing cross-sections of a conventional composite piezoelectric member 30.
Figure 1B:
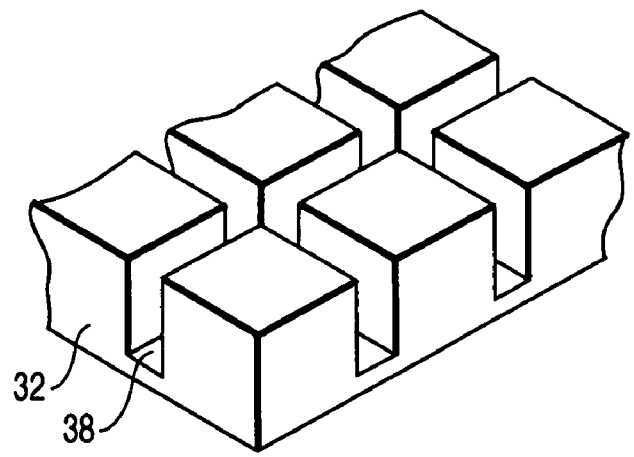
FIGS. 1B and 1C are explanatory views for chipping and cracking caused in a process of manufacturing the conventional composite piezoelectric member 30.
Figure 1C:
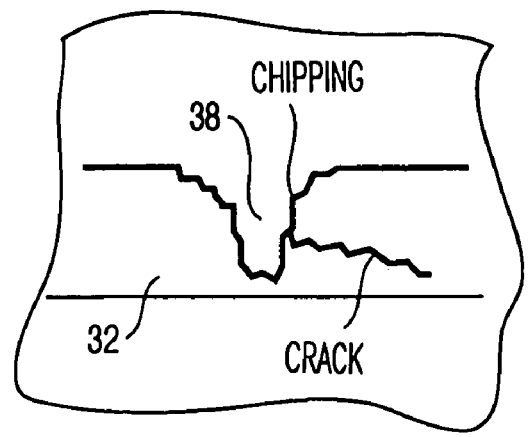
Figure 1D:
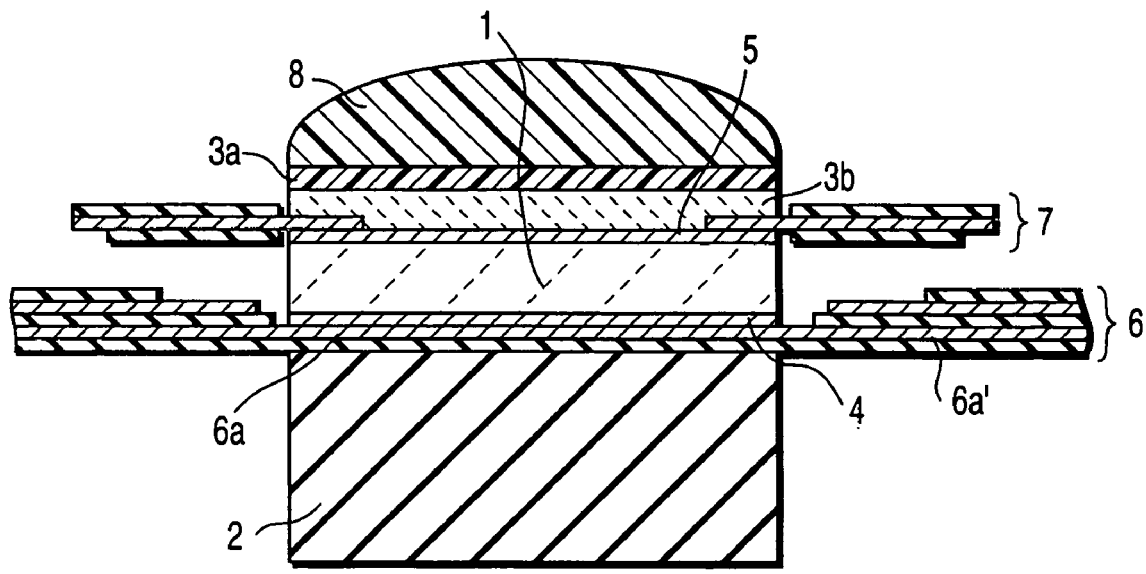
Figure 1E:
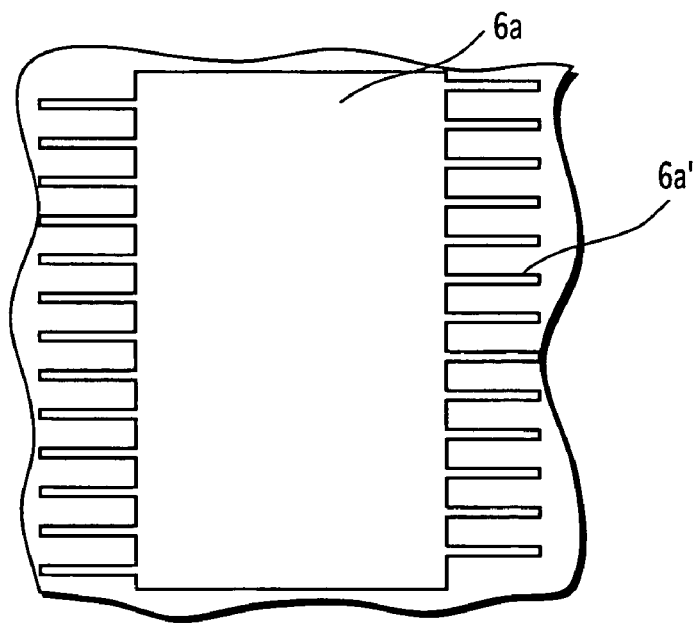
FIG. 1E shows a conductive layer of signal FPC 6 shown in FIG. 1D, viewed from the side of a single-crystal vibration element 1.
Figure 2:
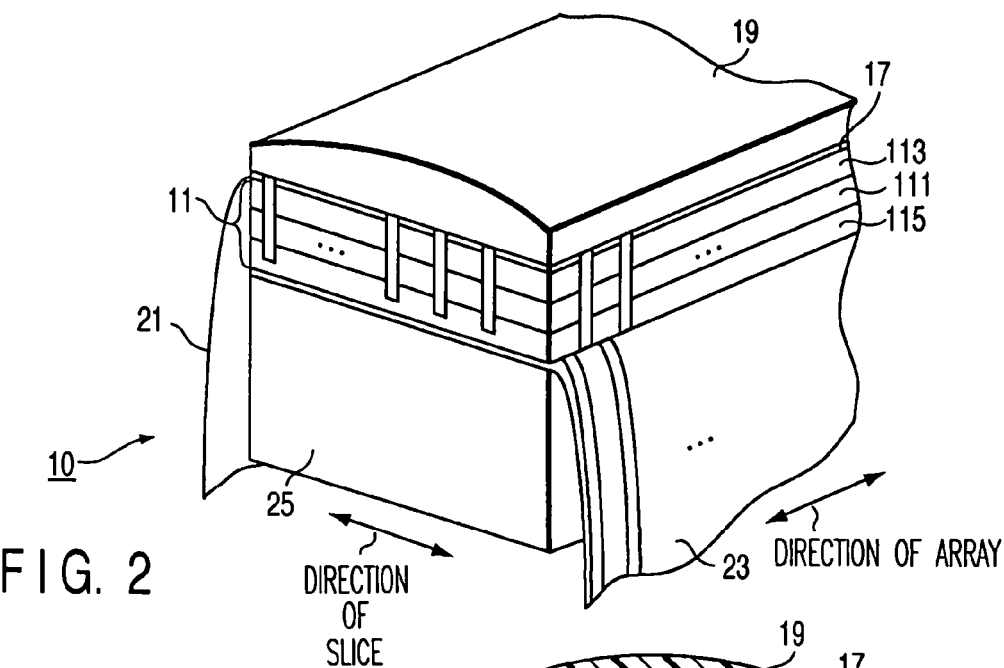
FIG. 2 is a perspective view showing a schematic structure of an ultrasonic probe 10 according to the first and second embodiments.

FIG. 2 shows a schematic structure of an ultrasonic probe 10 according to the first embodiment.

In FIG. 2, the ultrasonic probe 10 is constructed in a structure comprising a composite piezoelectric member (1-3 type) 11, an acoustic matching layer 17, an acoustic lens 19, a common electrode plate 21, a flexible wiring substrate 23, and a backing member 25.

The composite piezoelectric member (1-3 type) 11 includes a single-crystal piezoelectric member 111, an upper PVC resin layer 113, and a lower PVC resin layer 115. That is, the composite piezoelectric member (1-3 type) 11 is a piezoelectric member in which one-dimensional narrow rod made of single-crystal piezoelectric ceramics is embedded in a PVC resin matrix as a three-dimensional macro-molecule, and has a high electromechanical coupling factor and low acoustic impedance. Electrodes, which are not shown in the figure, for transmitting/receiving an electric signal based on a piezoelectric direct effect and a piezoelectric reverse effect are formed on both of the upper and lower sides of the composite piezoelectric member 11, by a method described later.

The single-crystal piezoelectric member 111 is solution-based single-crystal piezoelectric ceramics containing plumbum zinc niobate (PZN), plumbum titanate (PT), and the like, and is prepared in the manner described later.

The upper PVC resin layer 113 is a layer formed by applying PVC resins containing silver, to the side of the piezoelectric member 111 where an ultrasonic wave is irradiated (hereinafter called an upper side), and has conductivity, an excellent cutting characteristic, and smaller acoustic impedance (e.g., $2 \times 10^6$ to $10 \times 10^6$ g/m²s or so), compared with the single-crystal piezoelectric member.

The lower PVC resin layer 115 is a layer formed by applying PVC resins containing silver, to the side of the single-crystal piezoelectric member 111 (hereinafter called a lower side), which is opposite to the side described above, and also has conductivity, an excellent cutting characteristic, and smaller acoustic impedance, compared with the single-crystal piezoelectric member. The lower PVC resin layer 115 and the upper PVC resin layer 113 function to prevent occurrence of chipping and cracking in the single-crystal piezoelectric member 111. The method of forming the lower and upper PVC resin layers 115 and 113 will be specifically explained later.

The acoustic matching layer 17 is provided to be positioned between a test object not shown and the composite piezoelectric member 11, and is constructed by a single layer or multiple layers. The acoustic impedance can be matched between the test object and the composite piezoelectric member 11 by adjusting parameters such as an acoustic velocity, thickness, acoustic impedance, and the like.

The acoustic lens 19 is a lens made of silicon rubber or the like which has acoustic impedance close that of an organ, and improves the resolution by utilizing refraction of a sonic wave to converge an ultrasonic beam.

The common electrode plate 21 is provided at an end of the upper PVC resin layer 113. The common electrode plate 21 is an electrode for applying electric power to an electrode not shown but formed on the upper surface of the composite piezoelectric member 11 and connected to an earth.

The flexible wiring board 23 is provided at an end of the lower PVC resin layer 115, and is an electrode board having flexibility to apply electric power to each composite piezoelectric member 11.

The backing member 25 is provided on the back surface of the flexible wiring board 23 and mechanically supports the composite piezoelectric member 11. Also, the backing member 25 breaks the composite piezoelectric member 11 to shorten ultrasonic pulses. The thickness of this backing member 2 is maintained at a sufficient thickness (enough to damp) relative to the wavelength of the ultrasonic frequency to be used, in order to maintain excellent acoustic characteristics of the transducer.

Next, explanation will be made of a method of manufacturing the 1-3 type composite piezoelectric member 11 used for the ultrasonic probe 10 according to the first embodiment. The present manufacturing method can be divided into five large steps, i.e., preparation of a single-crystal piezoelectric member 111 (first step), formation of upper and lower PVC resin layers (second step), dicing of PVC resin layers 113 and 115 (third step), filling of resin (fourth step), and polishing of the PVC resin layers 113 and 115 (fifth step).

Explained first will be formation of the composite piezoelectric member 11 in the first step.

Plumbum zinc niobate (PZN) and plumbum titanate (PT) are put at a molecular ratio of 91:9 in a platinum vessel, together with Pb flux, and the temperature is increased to melt them. Thereafter, they are cooled to a room temperature to grow solution-based single-crystal. Thereafter, a Laue camera is used to attain <001> axis direction of the single-crystal, and the single-crystal is cut in a direction vertical to the axis. Further, the resultant is polished to the thickness of 300 μm, and thereafter, Ti/Au electrodes are formed on both surfaces by a sputtering method. The single-crystal piezoelectric member 111 can thus be prepared.

Explained next will be formation of the upper and lower PVC resin layers 113 and 115 in the second step.

The piezoelectric member 111 formed in the first step is temporarily fixed to a glass plate, and the periphery thereof is masked with a Kapton tape. Thereafter, conductive PVC resins containing silver are applied and polished to 300 μm by a plane polisher, thereby to form the upper PVC resin layer 113 having an excellent cutting characteristic. Similarly, the lower PVC resin layer 115 having a thickness of 300 μm and an excellent cutting characteristic is formed on the back surface side of the piezoelectric member 11. Note that the upper PVC resin layer 113 and the lower PVC resin layer 115 may be formed in a reverse order.

Explained next will be dicing of the upper PVC resin layer 113 and lower PVC resin layer 115 in the third step and the resin filling in the fourth step.

Kerfs having a depth of 800 μm at a pitch of 200 μm (uncut part of 100 μm) are cut, by a dicing saw with a blade having a thickness of 50 μm, in the piezoelectric member 111 sandwiched between the layers 113 and 115 made of PVC resins containing silver, which are formed in the second step. Further, epoxy resins are filled in the cut kerfs and hardened. Similarly, cut kerfs are formed in a direction perpendicular to the cut kerfs, and epoxy resins 12 are filled and hardened therein.

Explained next will be polishing of the upper and lower PVC resin layers 113 and 115 in the fifth step.

Thereafter, the member 111 is temporarily fixed to a glass plate, with the uncut side set as a lower surface, and the layer on the opposite side is polished to 150 μm by a plane polisher. Further, polishing is carried out to 150 μm, with the uncut side set as an upper surface. Further, Ti/Au electrodes are formed on both surfaces by sputtering, and thus, it is possible to form the 1-3 type composite piezoelectric member 11 with less chipping and cracking due to cutting and the like.

At last, an electric field of 1 KV/mm is applied to the 1-3 type composite piezoelectric member 11 formed by the above manufacturing method, thereby to perform polarization processing.

Note that the composite piezoelectric member manufacturing method described above can be variously modified without changing the essence of the method. For example, the present invention is applicable also to a 2-2 type composite piezoelectric member as will be explained in the second embodiment although explanation has been made with reference to a 1-3 type composite piezoelectric member 11 as an example. In addition, the member may firstly be cut into a matrix shape, and resins may then be filled therein. Further, in case of filling epoxy resins separately in two stages like the present embodiment, the kinds of the epoxy resins may be changed.

Next explanation will be made of an example of a method of manufacturing a one-dimensional array type ultrasonic probe 10 with use of a 1-3 type composite piezoelectric member manufactured by the manufacturing method described above, with reference to FIG. 3.

Figure 3:
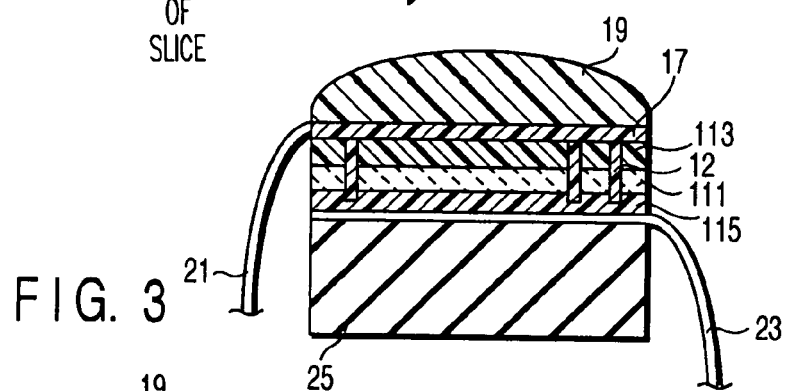
FIG. 3 is a view showing a cross-section of the ultrasonic probe 10 according to the first and second embodiments.

FIG. 3 is a view showing a cross-section of the ultrasonic probe 10 according to the present embodiment.

At first, a common electrode plate 21 is connected to the upper PVC resin layer 113 of the composite piezoelectric member 11, and a flexible wiring board 23 is connected to the lower PVC resin layer 115, with use of conductive paste, thereby to form a second acoustic matching layer 17 in the side of the ultrasonic wave radiation surface. Thereafter, a backing member 25 and the flexible wiring board are adhered to each other by epoxy resins.

Next, cutting is carried out at a pitch of 200 μm in the array direction by a dicing saw with a blade having a thickness of 50 μm. A silicon-based adhesion is filled in the kerfs, and an acoustic lens 19 is adhered.

Further, a coaxial cable having a electrostatic capacity of 110 pF/m and a length of 2 m is connected to the flexible wiring board 23, and thus, a one-dimensional array type ultrasonic probe 10 can be manufactured.

Next explanation will be made of effects and operation caused by the ultrasonic probe manufactured in the method described above.

In the ultrasonic probe 10, a single-crystal piezoelectric member 111 is sandwiched between the upper PVC resin layer 113 and the lower PVC resin layer 115 in the 1-3 type composite piezoelectric member 11. It is therefore possible to prevent occurrence of chipping even during formation of array-like kerfs.

In addition, the upper PVC resin layer 113 and the lower PVC resin layer 115 have smaller acoustic impedance compared with the single-crystal piezoelectric member 111, conductivity, and an excellent cutting characteristic, and can therefore serve as electrodes for transmitting/receiving an electric signal concerning the single-crystal piezoelectric member 111 or acoustic matching layers.

After formation of array-like kerfs and filling of epoxy resins 12 are completed through the first to fourth steps, i.e., after there is no possibility to cause chipping, at least one of the upper PVC resin layer 113 and the lower PVC resin layer 115 may be all polished and an electrode or an acoustic matching layer may be newly provided in the fifth step.

The upper PVC resin layer 113 and the lower PVC resin layer 115 should preferably have hardness of 700 to 1000 HDd according to a duro-meter.

According to the structure of this kind, processing errors during cutting can be reduced so that an ultrasonic probe with high sensitivity and a wide band can be manufactured easily, by providing an excellent cutting characteristic according to the present invention to at least one of the upper and lower surfaces of solution-based piezoelectric single-crystal. In addition, since the PVC resin layers have conductivity, excellent electric connection to the single-crystal piezoelectric member is achieved so that an ultrasonic vibration element with an excellent characteristic can be formed.

SECOND EMBODIMENT

In the first embodiment, explanation will be made of a method of manufacturing a 1-3 type composite piezoelectric member 11 and a method of manufacturing an ultrasonic probe 10 using the piezoelectric element. In contrast, in the second embodiment, explanation will be made of a method of manufacturing a 2-2 type composite piezoelectric member and a method of manufacturing an ultrasonic probe using the 2-2 type composite piezoelectric member.

Since the outer appearance of the ultrasonic probe using the 2-2 type composite piezoelectric member is the same as that of the ultrasonic probe 10 using the 1-3 type composite piezoelectric member shown in FIG. 3, the same figure will be also used and explanation of those components that have already been explained will be omitted herefrom. In addition, explanation of those parts that overlap the manufacturing methods explained in the first embodiment will be also omitted and only the different parts will be explained below.

The method of manufacturing a 2-2 type composite piezoelectric member according to the second embodiment adopts the same steps as the first and second steps of the first embodiment.

Explanation will now be made of dicing of the upper PVC resin layer 113 and the lower PVC resin layer 115 in the third step and filling of resins in the fourth step.

Kerfs having a depth of 800 µm (100 m uncut) are cut at a pitch of 200 µm in the array direction and a direction vertical to the array direction, by a dicing saw with a blade having a thickness of 50 µm, in a piezoelectric member 11 sandwiched between PVC resin layers 3 and 4 containing silver, which are formed in the second step. Thereafter, epoxy resins 12 are filled and hardened in the cut kerfs.

Next explanation will be made of polishing of the upper and lower PVC resin layers 113 and 115 in the fifth step.

Thereafter, the member is temporarily fixed to a glass plate with the uncut side set as a lower surface, and the layer in the opposite side is polished to 150 µm by a plane polisher. Further, the uncut side set as an upper side is also polished to 150 µm. Further, Ti/Au electrodes are formed on both surfaces by sputtering, and thus, a 2-2 type composite piezoelectric member 11 which includes less chipping and cracking caused by cutting and the like can be formed.

At last, an electric field of 1 KV/mm is applied to the 2-2 type composite piezoelectric member 11 formed in the manufacturing method described above, thereby to perform polarization processing.

Next explanation will be made of an example of a method of manufacturing a one-dimensional array type ultrasonic probe 10 with use of a 2-2 type composite piezoelectric member manufactured in the method described above.

At first, a common electrode plate 21 is connected to the upper PVC resin layer 113 of the composite piezoelectric member 11, and a flexible wiring board 23 is connected to the lower PVC resin layer 115, with use of conductive paste, thereby to form a second acoustic matching layer 17 in the side of the ultrasonic wave radiation surface. Thereafter, this structure is adhered to a backing member 25 by epoxy resins.

Next, cutting is carried out at a pitch of 200 µm in the array direction by a dicing saw with a blade having a thickness of 50 µm. A silicon-based adhesion is filled in the kerfs, and an acoustic lens 6 is adhered.

Further, a coaxial cable having an electrostatic capacity of 110 pF/m and a length of 2 m is connected to the flexible wiring board 23, and thus, a one-dimensional array type ultrasonic probe 10 can be manufactured.

According to the ultrasonic probe having the 2-2 type composite piezoelectric member manufactured in the method described above, it is possible to attain the same functions and advantages as those of the ultrasonic probe having the 1-3 type composite piezoelectric member explained in the first embodiment.

THIRD EMBODIMENT

In the third embodiment, explanation will be made of a method of manufacturing a two-dimensional array type ultrasonic probe in which ultrasonic vibration elements are two-dimensionally arrayed (e.g., in a matrix-like array) with use of a 1-3 type composite piezoelectric member 11.

Figure 4:
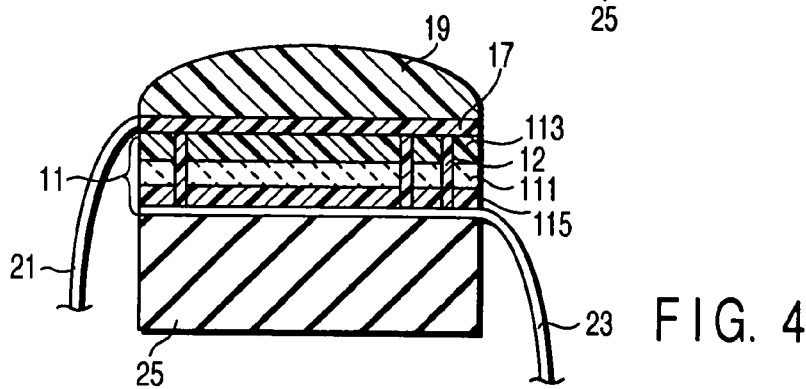
FIG. 4 is a lateral cross-sectional view of a two-dimensional array type ultrasonic probe 30 according to the third embodiment.

FIG. 4 is a lateral cross-sectional view of a two-dimensional array type ultrasonic probe 30 according to the third embodiment.

Those components that have already been explained with reference to FIG. 3 are denoted at common reference symbols and explanation thereof will be omitted herefrom. In addition, explanation of those parts that overlap the manufacturing methods described in the first and second embodiments will be omitted herefrom, and only different parts will be explained below.

In the method of manufacturing a 1-3 type composite piezoelectric member 11 according to the third embodiment, the first and second steps are the same as those of the first embodiment.

Explained next will be dicing of the upper PVC resin layer 113 and the lower PVC resin layer 115 in the third step and filling of resins in the fourth step.

Kerfs having a depth of 800 µm (100 µm uncut) are cut like an array at a pitch of 200 Um, by a dicing saw with a blade having a thickness of 50 µm, in a piezoelectric member 11 sandwiched between PVC resin layers 3 and 4 containing silver, which are formed in the second step. Epoxy resins 12 are filled and hardened in the cut kerfs. Likewise, similar cut kerfs are formed vertically to the cut kerfs described above, and epoxy resins 12 are also filled and hardened therein.

Thereafter, the member is temporarily fixed to a glass plate with the uncut side set as a lower surface, and the layer in the opposite side is polished to 150 µm by a plane polisher. Further, the uncut side set as an upper side is also polished to 150 µm. That is, the lower PVC resin layer 113 in the uncut side is divided even after this polishing.

Further, Ti/Au electrodes are formed on both surfaces by sputtering, and thus, a 1-3 type composite piezoelectric member 11 which includes less chipping and cracking caused by cutting and the like can be formed.

Next explanation will be made of an example of a method of manufacturing a two-dimensional array type ultrasonic probe 30 with use of a composite piezoelectric member having a two-dimensional array, which is manufactured by the method described above.

At first, a common electrode plate 21 is connected to the upper PVC resin layer 113 in the uncut side, and a flexible wiring board 8 provided with a two dimensional signal wiring is connected to the opposite surface throughout the overall surface. A second acoustic matching layer 19 is formed in the side of the ultrasonic wave radiation surface and is thereafter adhered to a backing member 25 by epoxy resins. A silicon-based acoustic lens 19 is adhered thereto. Uniformly in the signal side of the FPC, a voltage of 1 KV/mm is applied between the signal side and the ground side.

Further, a coaxial cable having an electrostatic capacity of 110 pF/m and a length of 2 m is connected to the flexible wiring board 8, and thus, a two-dimensional array type ultrasonic probe 30 can be manufactured.

The above explanation deals with a two-dimensional array type ultrasonic probe 30 using a 1-3 type composite piezoelectric member. The present invention, however, is applicable to a 2-2 type composite piezoelectric member.

Accordingly, the two-dimensional array type ultrasonic probe 30 having the 1-3 type composite piezoelectric member according to the third embodiment can attain the same functions and advantages as those of the one-dimensional array type ultrasonic probes explained in the first and second embodiments.

FOURTH EMBODIMENT

The fourth embodiment explains another method of manufacturing a composite piezoelectric member 11 of 1-3 or 2-2 type.

At first, another method of manufacturing a 1-3 type composite piezoelectric member 11 will be explained.

A single-crystal piezoelectric member 111 is prepared in the same manner as that of the first step shown in the first embodiment.

In the subsequent second step, upper and lower PVC resin layers 113 and 115 are formed as follows, according to the present embodiment. That is, a plurality of piezoelectric members 111 formed in the first step are arranged on and adhered to a conductive resin sheet. This sheet is cut out into a size of the back surface of the piezoelectric member 11. Used as the conductive resin sheet is PVC resin containing conductive silver, which is molded into a sheet-like shape.

Subsequently, a 1-3 type composite piezoelectric member 11 is formed through the same steps as the third, fourth, and fifth steps shown in the first embodiment. Polarization processing is performed on the 1-3 type composite piezoelectric member 11 thus formed, by applying an electric field of 1 KV/mm.

According to the manufacturing method described above, it is also possible to form a 1-3 type composite piezoelectric member 11 described in the first embodiment. In addition, the present manufacturing method is practically advantageous in case of increasing the size of an ultrasonic probe using piezoelectric single-crystal. That is, it is generally difficult to increase the size of the piezoelectric single-crystal itself, and therefore, it is not easy to increase the size of the ultrasonic probe using a composite piezoelectric member made of piezoelectric single-crystal. Particularly according to the present manufacturing method, however, it is possible to manufacture a 1-3 type composite piezoelectric member 11 in which, for example, single-crystal piezoelectric members 111 are arranged in array directions, by arranging a plurality of single-crystal piezoelectric members 111 on a conductive resin sheet. The ultrasonic probe can thus easily be enlarged.

Next, explanation will be made of another method of manufacturing a 2-2 type composite piezoelectric member 11. In the 2-2 type composite piezoelectric member 11, a 2-2 type composite piezoelectric member can be formed of a single-crystal piezoelectric member adhered to a conductive resin sheet in the same procedure as that of the method of manufacturing the composite piezoelectric member 11 of the 1-3 type described above. The other steps are the same as those of the second embodiment.

A one- or two-dimensional array type ultrasonic probe using a 1-3 or 2-2 type composite piezoelectric member formed in each of the manufacturing methods described above can be manufactured in a conventional method.

FIFTH EMBODIMENT

In the fifth embodiment, explanation will be made of another one- or two-dimensional array type ultrasonic probe using a 1-3 or 2-2 type composite piezoelectric member 11.

Figure 5:
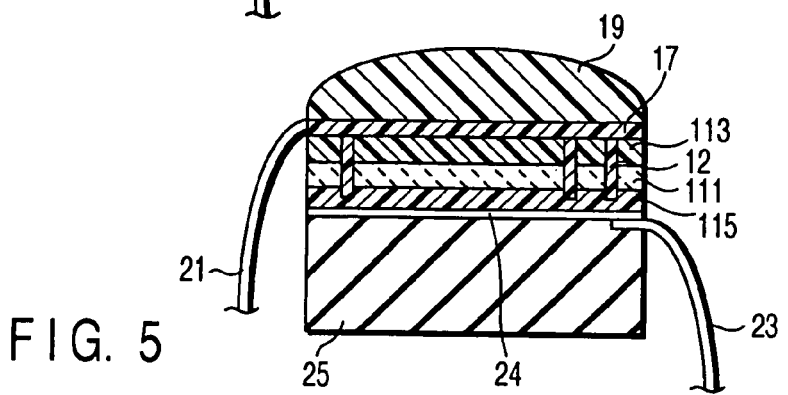
FIG. 5 shows a schematic structure of an array type ultrasonic probe according to the fifth embodiment.

FIG. 5 shows a schematic structure of an array type ultrasonic probe according to the present embodiment. The present embodiment differs from the probe shown in FIG. 4 in that an electrode 24 is provided at the lower PVC resin layer 115 of each single-crystal piezoelectric member 111 and a flexible wiring board 23 is led from an end of the electrode 24. In the structure of this kind, it is possible to attain the same functions and advantages as those of the array type ultrasonic probes explained in the first to third embodiments.

SIXTH EMBODIMENT

In the sixth embodiment, explanation will be made of a one-dimensional array type ultrasonic probe which reduces chipping and cracking, without forming the lower or upper PVC resin layer.

At first, the schematic structure of a one-dimensional array type ultrasonic probe 35 according to the present embodiment will be explained with reference to FIGS. 6 and 7.

Figure 6:
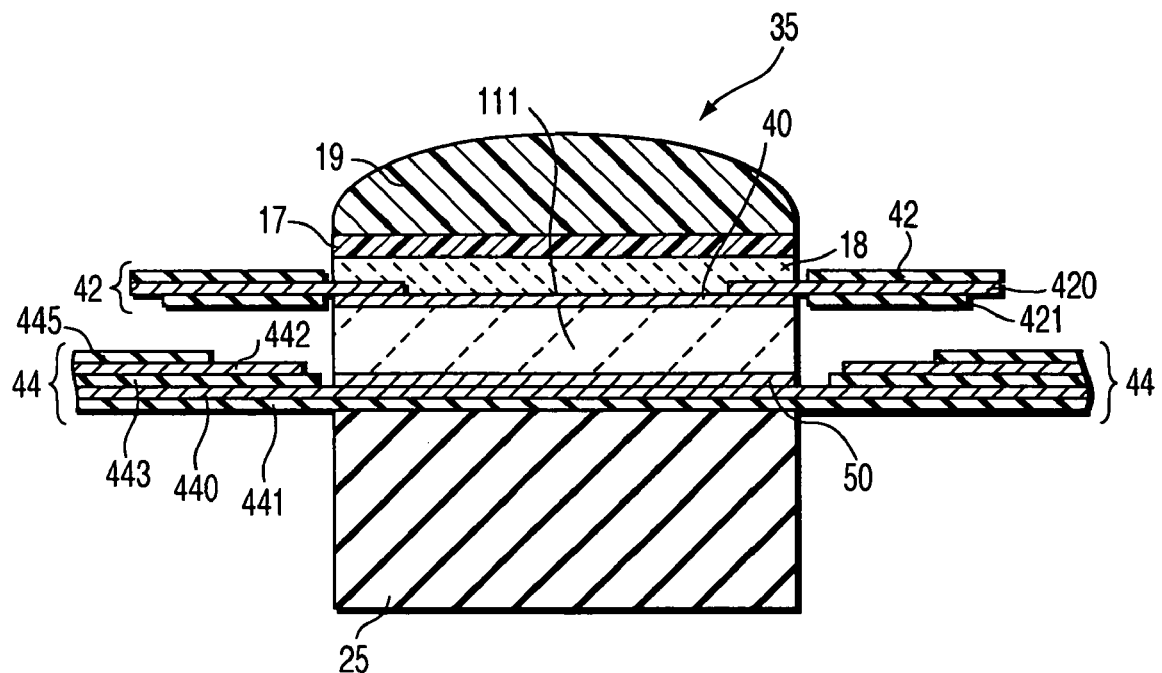
FIG. 6 shows a cross-section of an array type ultrasonic probe 35 according to the sixth embodiment.

FIG. 6 shows a cross-sectional view of the one-dimensional array type ultrasonic probe 35 according to the present embodiment.

As shown in FIG. 6, a first electrode 40 is provided on the upper surface of each single-crystal piezoelectric member 111, and a second electrode 50 is provided on the lower surface thereof. Each first electrode 40 is connected with a first flexible wiring board 42 by conductive paste. Meanwhile, each second electrode 50 is connected with a second flexible wiring board 44 by an epoxy-based adhesion.

A predetermined electric power is applied to or detected from the electrodes 40 and 50 through the flexible wiring boards 42 and 44, respectively. The first flexible wiring board 42 is a multi-layer board comprised of a conductive layer 420 made of copper or the like and an insulating layer 421 made of a polyimide film or the like, and serves to make ground connection. Also, the second flexible wiring board 44 is a multi-layer board comprised of conductive layers 440 and 442 made of copper or the like, and insulating layers 441, 443, and 445 made of polyimide films or the like, and electrically connects the probe 35 with the body of an ultrasonic diagnosis apparatus. Note that the conductive layer 440 has a predetermined wiring pattern described later (see FIG. 7).

The one-dimensional array type ultrasonic probe 35 has a first acoustic matching layer 17 and a second acoustic matching layer 18. The array pitch of vibration elements of this probe 35 is about 0.1 mm in case where it is narrow.

Figure 7:
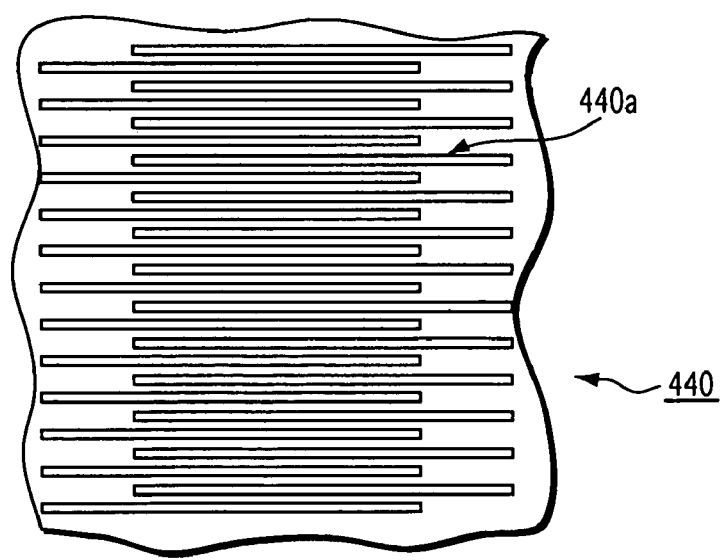
FIG. 7 shows a top view of a conductive layer 440 of a second flexible wiring board 44.

FIG. 7 shows a top view of the conductive layer 440 of the second flexible wiring board 44.

As shown in FIG. 7, the second flexible wiring board 44 has a wire 440a having a predetermined pattern. The pitch width of the wire 440a is equal to or smaller than the pitch width of the array arrangement of the single-crystal piezoelectric members 111. Wires 440a are respectively adhered to the entire surfaces of the second electrodes corresponding to the single-crystal piezoelectric members 111, by an epoxy-based adhesion, and are led in directions which are alternately opposed to each other, as shown in FIG. 7. Alternative leading of these wires are not always necessary but may be a structure in which all wires are led in one same direction.

In the present embodiment, the same board as the second flexible wiring board 44 is used for the first flexible wiring board 42.

According to this kind of probe 35, the first and second flexible wiring boards 42 and 44 are set at a pitch width equal to or smaller than that of the array arrangement of the single-crystal piezoelectric members 111. Therefore, in cutting for forming an array arrangement, the conductive layer 440 and the single-crystal piezoelectric member 111 need not be cut simultaneously. That is, since the conductive layer 440 and the single-crystal piezoelectric member 111 which have cutting characteristics different from each other are not cut simultaneously, it is possible to restrict occurrence of cracking and chipping in manufacture of arrays. Also, occurrence of cracking and chipping can be restricted by cutting the single-crystal piezoelectric member 111 with the first flexible wiring boards 42 and the second flexible wiring boards 44 connected.

According to experiments made by the present inventors, no disconnected element existed and a variant of the sensitivity was as small as 2 dB when the characteristics of a completed probe 35 were evaluated.

In contrast, in case of a conventional method in which, for example, the conductive layer 440 of the second flexible wiring board 44 was extended to the size of the contact surface of the single-crystal piezoelectric member 111 and was joined to the overall surface of the single-crystal piezoelectric member 111, evaluation made by the present inventors was as follows. That is, cracking occurred at a rate of about 30% in array processing. After completion of a probe, characteristic evaluation was made to find that disconnected elements appeared at a rate of about 20% and variants of the sensitivity were as large as 10 dB. Causes of the disconnection were investigated to find that cracks which are considered to have been created during array processing existed in the vibration element of the channel which causes a disconnection. Also, chipping appeared in many vibration elements. These results are considered to have influenced variants of the sensitivity.

From the viewpoint of mass-production of probes, there is a case that the same board as the second flexible wiring board 44 need not be used for the first flexible wiring board 42. This is because the wire 442 of each flexible wiring board is patterned at a width equal to or smaller than that of the single-crystal piezoelectric members 111 arranged in an array, and therefore, it is not easy to make positioning between the first flexible wiring board 42 and the second flexible wiring board 44.

Hence, the structure may be arranged such that the conductive layer shown in FIG. 7 is used only for the second flexible wiring board 44. According to the structure of this kind, those conductive layers that are near end parts of the vibration elements of the first flexible wiring boards 42 need to be cut, and therefore, influences thereof are negligible so that cracking or chipping does not occur during processing. According to evaluation made by the present inventors, the probe 53 does not include a disconnected element at all and variants of the sensitivity are as small as 2 dB.

Note that the ultrasonic probe 35 according to the present embodiment is not limited to the structure described above. For example, following modifications can be made.

Figure 8:
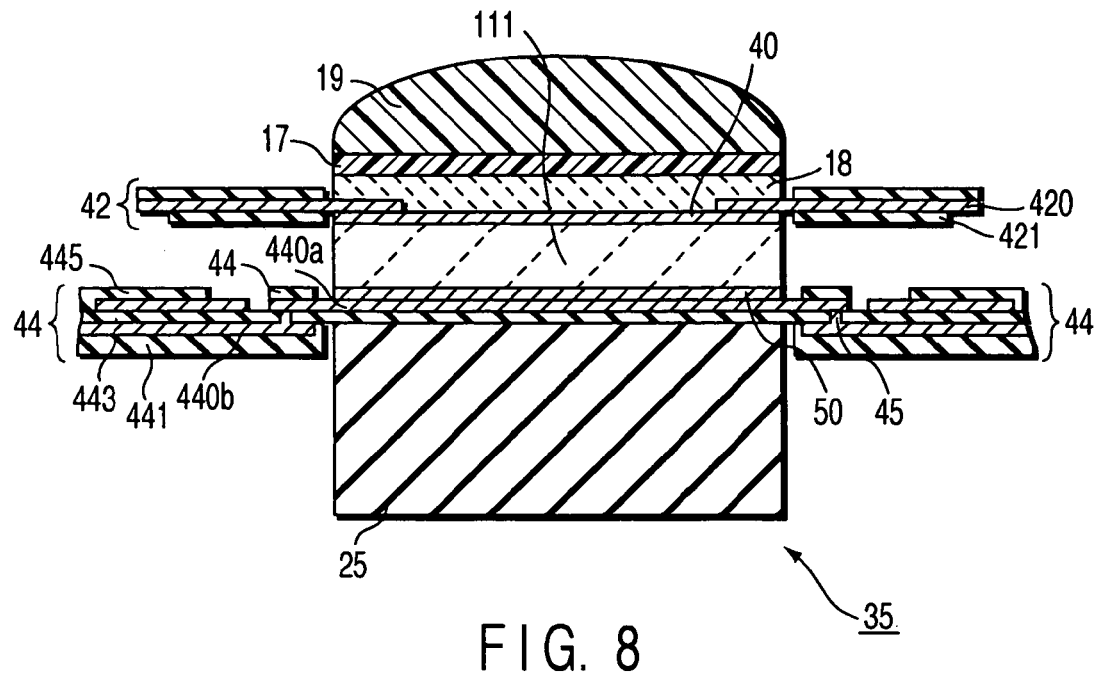
FIG. 8 is an explanatory view for a modification example of an ultrasonic probe 35.
Figure 9:
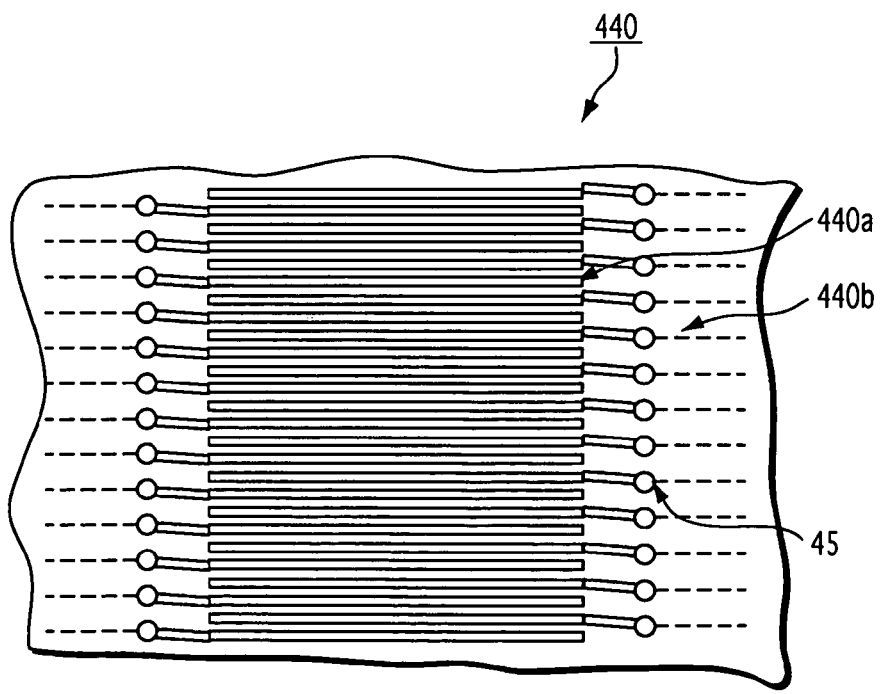
FIG. 9 is a view showing a pattern wire of a second flexible wiring board 44 which the ultrasonic probe 35 according to the modification examples has.

FIG. 8 is an explanatory view for a modification example of the ultrasonic probe 35. FIG. 9 is a view showing a pattern wire of the second flexible wiring board which the ultrasonic probe 35 according to the present modification example has.

In FIG. 8, the ultrasonic probe 35 has a through-hole in addition to the structure shown in FIG. 6. Electric conductance between the wires 440a and 440b of the conductive layer 440 is attained by this through hole 45.

According to the ultrasonic probe 35 according to the present embodiment described above, chipping and cracking can be reduced.

SEVENTH EMBODIMENT

In the seventh embodiment, explanation will be made of an ultrasonic probe in which wires led from the first electrode 40 and the second electrode 50 are integrated together and are led from the lower surface of the single-crystal piezoelectric member 111.

Figure 10:
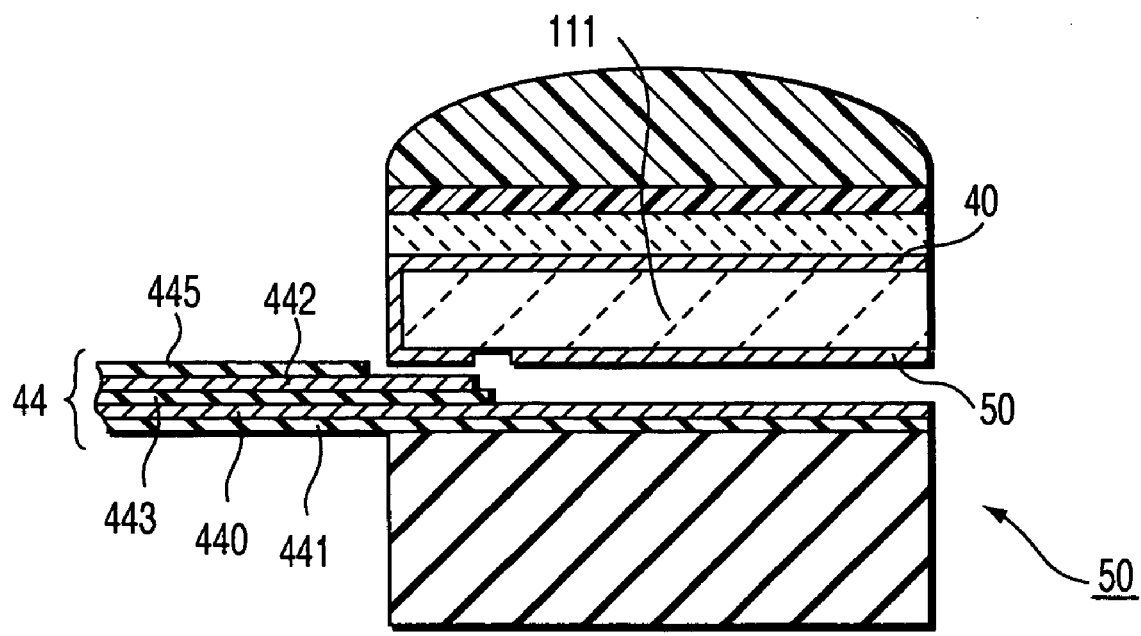
FIG. 10 is an explanatory view for the schematic structure of an ultrasonic probe 50 according to the seventh embodiment.

FIG. 10 is an explanatory view for the schematic structure of an ultrasonic probe 50 according to the seventh embodiment. Note that this figure shows a condition before the first electrode 40 and the second electrode 50 are adhered to the second flexible wiring board 44. In FIG. 10, the first electrode 40 for ground is a detour electrode which continues from the upper surface of the single-crystal piezoelectric member 111 through a side surface thereof to the lower surface thereof. The first electrode 40 is connected to a conductive layer 442 of the second flexible wiring board 44, and the second electrode 50 is connected to a conductive layer 440 of the second flexible wiring board 44. Note that an exposed part is provided for each of the conductive layers 442 and 440, in consistence with each of the electrodes 40 and 50 of the single-crystal piezoelectric member 111.

Each of the conductive layers 440 and 442 has a thickness of 18 μm. The insulating layer 443 made of polyimide has a thickness of 12.5 to 25 μm.

Next, a modification example of the ultrasonic probe 50 will be explained.

Figure 11:
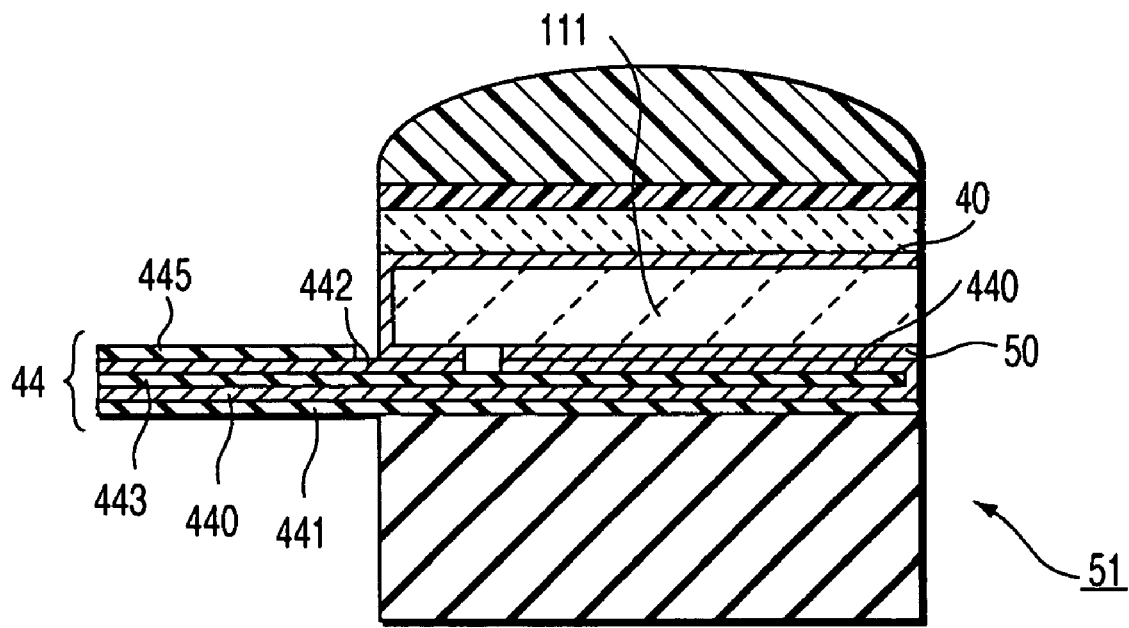
FIGS. 11, 12, and 13 are views showing modification examples of the ultrasonic probe according to the seventh embodiment.

FIG. 11 is a view showing an ultrasonic probe 51 as a modification example of the ultrasonic probe 50. As shown in FIG. 11, the conductive layer 442 is extended and connected to the first electrode 40 detoured around the single-crystal piezoelectric member 111. The detour structure can be formed by a method of galvanizing an end part or so.

Compared with the ultrasonic probe 50 shown in FIG. 10, a gap is eliminated between the conductive layer 442 and the conductive layer 440 of the probe 51 shown in FIG. 11. Therefore, with this structure, it is possible to prevent breakdown of the single-crystal piezoelectric member 111 which can be caused by pressed adhesion.

Figure 12:
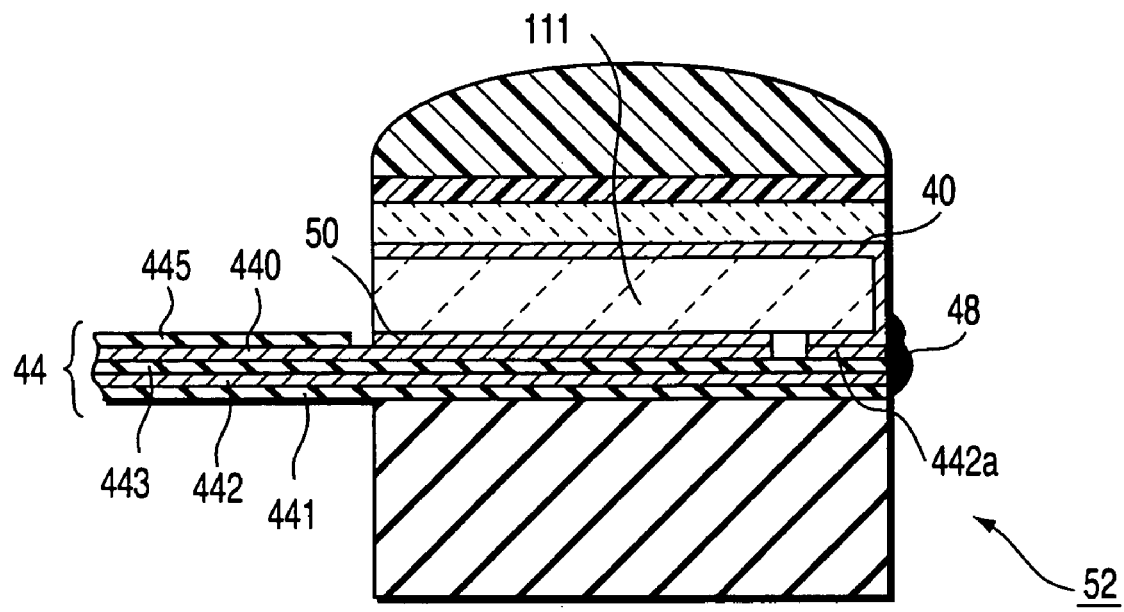

FIG. 12 is a view showing an ultrasonic probe 52 as a modification example of the ultrasonic probe 51. The probe 52 shown in FIG. 12 is practically advantageous in case where the detour structure of the conductive layer is difficult to create in the form of the probe 51 shown in FIG. 11. As shown in FIG. 12, the vertical positional relationship between the conductive layer 440 and the conductive layer 442 is reversed from that of the case shown in FIG. 11. Also, the position of the detour structure of the first electrode 40 is reversed from that of the probe 51. Electric conductance between the first electrode 40 and the conductive layers 442 and 442a is made by a conductive member 48.

With this structure, the first electrode 40 may be connected with the conductive layers 442 and 442a by the conductive member 48 after adhering the single-crystal piezoelectric member 111 and the second flexible wiring board 44 to each other. The conductive member should preferably be conductive paste. Also, connection based on the conductive member 48 may be made after forming an ultrasonic vibration element array.

Figure 13:
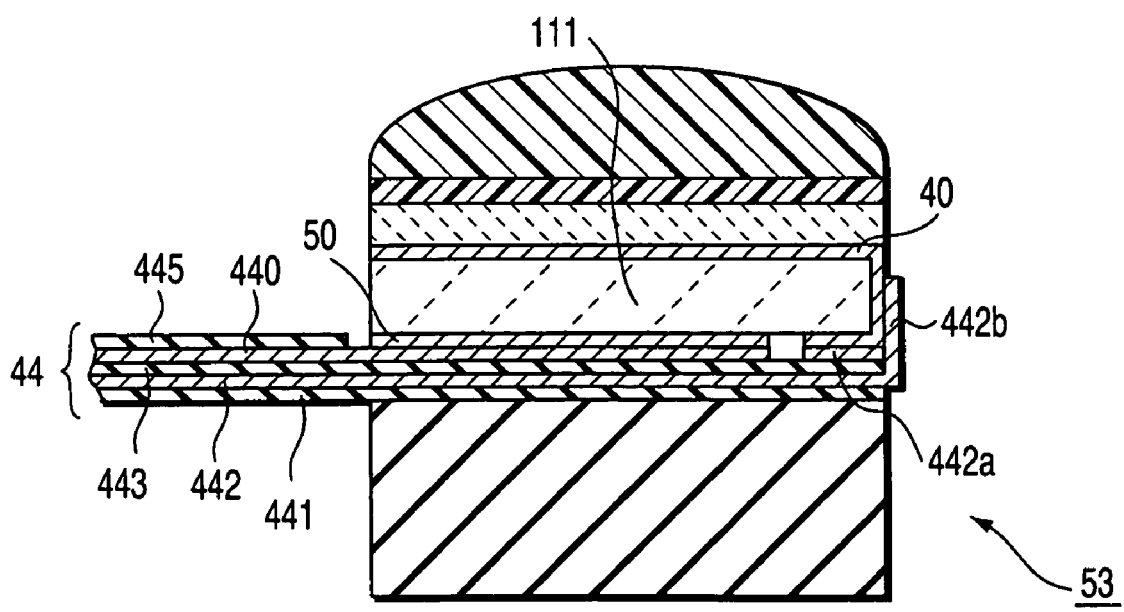

FIG. 13 is a view showing an ultrasonic probe 53 as a modification example of the ultrasonic probe 52. In the ultrasonic probe 53 as shown in FIG. 13, an exposed part 442b is exposed from a top end of the conductive layer 442, and the exposed part 442b is bent to connect with the first electrode 40 after adhering the single-crystal piezoelectric member 111. In this kind of structure, more stable connection can be attained.

If each of the first flexible wiring boards 42 shown in FIGS. 11, 12, and 13 is constructed in a structure including a pattern wire 440a having a pitch width equal to or smaller than that of the array arrangement of the single-crystal piezoelectric member 111 which the probe 35 has, Like the second flexible wiring board 44, it is possible to prevent cracking and chipping during processing. This is because the conductive layers having a deteriorated cutting characteristic and the single-crystal piezoelectric member 111 are not cut together.

Additional advantages and modifications will readily occur to those skilled in the art. Therefore, the present invention in its broader aspects is not limited to the specific details, representative devices, and illustrated examples shown in described herein. Accordingly, various modifications may be made without departing from the spirit or scope of the general inventive concept as defined by the appended claims and their equivalents.

For example, the single-crystal piezoelectric member used in each of the embodiments is not limited particularly. For example, it may be of a composite perovskite type including at least plumbum titanate, like single-crystal made of a solid solution of plumbum zinc niobate represented by $Pb((Zn1/3Nb2/3)0.91Ti00.09)03$ and plumbum titanate, and single-crystal made of a solid solution of plumbum magnesium niobate and plumbum titanate, single-crystal made of a solid solution of plumbum scandium niobate and plumbum titanate, and the like can be cited. Alternatively, single-crystal of lithium niobate, potassium niobate, or the like may be used.

According to the above-described invention of the first to third embodiments, occurrence of chipping is prevented by forming PVC resin layers on the upper and lower surfaces of a single-crystal piezoelectric member 111, and further, a function as an electrode or acoustic matching layer is provided, thereby to realize an ultrasonic probe having a high sensitivity and a wide band. However, even if the PVC resin layer is formed on one surface of the single-crystal piezoelectric member 111, it can prevent occurrence of chipping and functions as an electrode or acoustic matching layer.

What is claimed is:

1. An ultrasonic probe comprising:
   a plurality of piezoelectric members formed of solution-based single-crystal containing at least plumbum titanate, and arranged like an array;
   a plurality of first electrodes formed on lower surfaces of the piezoelectric members, the lower surface being an opposite side of an acoustically emitting side; and
   a first flexible printed wiring board having a plurality of pattern wires having a width smaller than a width of each of the piezoelectric members in an array direction, extending in a longitudinal direction of each of the piezoelectric members, and configured to lead and connect the first electrodes to an ultrasonic diagnosis apparatus body.

2. The ultrasonic probe according to claim 1, further comprising:
   a plurality of second electrodes formed on upper surfaces of the piezoelectric members; and
   a second flexible printed wiring board including a plurality of second pattern wires having a width smaller than a width of each of the piezoelectric members in an array direction, and configured to lead and connect the second electrode to ground.

3. The ultrasonic probe according to claim 1, further comprising an upper resin layer which is formed on an upper surface of the piezoelectric member, the upper surface being the acoustically emitting side, and which has smaller acoustic impedance than the piezoelectric member, and a cutting characteristic and electrical conductivity so as to function as an electrode.

4. An ultrasonic probe comprising:
   a plurality of piezoelectric members formed of solution-based single-crystal comprising at least plumbum titanate, and arranged like an array;
   a plurality of first electrodes formed on lower surfaces of the piezoelectric members;
   a first flexible printed wiring board having a plurality of pattern wires having a width smaller than a width of each of the piezoelectric members in an array direction, extending in a longitudinal direction of each of the piezoelectric members, and configured to lead and connect the first electrodes to an ultrasonic diagnosis apparatus body;
   a plurality of second electrodes formed on upper surfaces of the piezoelectric members; and
   a second flexible printed wiring board including a plurality of second pattern wires having a width smaller than a width of each of the piezoelectric members in an array direction, leading and connecting the electric wires to ground.

5. The ultrasonic probe according to claim 4, wherein the plurality of first pattern wires included in the second flexible printed wiring board extend along an entire length of each of the piezoelectric members.

6. An ultrasonic probe comprising:
   a plurality of single-crystal piezoelectric members;
   a plurality of lower resin layers which are formed on lower surfaces of the piezoelectric members and which have smaller acoustic impedance than the piezoelectric members, a cutting characteristic and electrical conductivity so as to function as electrodes, an acoustic impedance of $2\times10^6$ $g/m^2$ to $10\times10^6$ $g/m^2$ so as to function as acoustic matching layers, the lower surfaces being an opposite side of an acoustically emitting side; and
   a first flexible printed wiring board having a plurality of pattern wires having a width smaller than a width of each of the piezoelectric members in an array direction, extending in a longitudinal direction of each of the piezoelectric members, and configured to lead and connect the first electrodes to an ultrasonic diagnosis apparatus body.

7. The ultrasonic probe according to claim 6, further comprising an upper resin layer which is formed on an upper surface of the piezoelectric member, the upper surface being the acoustically emitting side, and which has smaller acoustic impedance than the piezoelectric member, a cutting characteristic and electrical conductivity so as to function as an electrode, an acoustic impedance of $2\times10^6$ $g/m^2$ to $10\times10^6$ $g/m^2$ and functions as an acoustic matching layer.

8. An ultrasonic probe comprising:
   a plurality of 1-3 or 2-2 type composite piezoelectric members formed of solution-based single-crystal comprising at least plumbum titanate,
   a plurality of lower resin layers which are formed on lower surfaces of the piezoelectric members and which have smaller acoustic impedance than the piezoelectric members, a cutting characteristic and electrical conductivity so as to function as electrodes, an acoustic impedance of $2\times10^6$ $g/m^2$ to $10\times10^6$ $g/m^2$ so as to function as acoustic matching layers; and
   a first flexible printed wiring board having a plurality of pattern wires having a width smaller than a width of each of the piezoelectric members in an array direction, extending in a longitudinal direction of each of the piezoelectric members, and configured to lead and connect the first electrodes to an ultrasonic diagnosis apparatus body.

9. An ultrasonic probe comprising:
a plurality of single-crystal piezoelectric members,
a plurality of lower resin layers which are formed on lower surfaces of the piezoelectric members and which have smaller acoustic impedance than the piezoelectric members, a cutting characteristic and electrical conductivity so as to function as electrodes, the lower surfaces being an opposite side of an acoustically emitting side; and
a plurality of wires which are arranged on the lower resin layers, extend along an entire length of each of the piezoelectric members and are connected to the lower resin layers along the longitudinal direction of each of the piezoelectric members.

10. An ultrasonic probe comprising:
a plurality of 1-3 or 2-2 type composite piezoelectric members formed of solution-based single-crystal containing at least plumbum titanate;
a plurality of lower resin layers which are formed on lower surfaces of the piezoelectric members and which have smaller acoustic impedance than the piezoelectric members, a cutting characteristic and an electrical conductivity so as to function as electrodes, the lower surfaces being an opposite side of an acoustically emitting side; and
a plurality of wires which are arranged on the lower resin layers, extend along an entire length of each of the piezoelectric members and are connected to the lower resin layers along the longitudinal direction of each of the piezoelectric members.

* * * * *